United States Patent [19]
Almon

[11] Patent Number: 5,217,112
[45] Date of Patent: Jun. 8, 1993

[54] VOLTAMETRIC ANALYSIS APPARATUS AND METHOD

[76] Inventor: Amy C. Almon, 410 Waverly Dr., Augusta, Ga. 30909

[21] Appl. No.: 754,841

[22] Filed: Sep. 4, 1991

[51] Int. Cl.⁵ ............................................. G01N 27/416
[52] U.S. Cl. ................................. 204/153.1; 204/412
[58] Field of Search ............ 204/412, 404, 400, 153.1, 204/153.11; 324/425

[56] References Cited

U.S. PATENT DOCUMENTS

| | | | |
|---|---|---|---|
| 2,531,747 | 11/1950 | Stearn | 204/195 |
| 3,428,532 | 2/1969 | Banks | 204/1 |
| 3,556,950 | 1/1971 | Dahms | 204/1 |
| 3,714,012 | 1/1973 | Herron | 204/195 |
| 3,859,193 | 1/1975 | Bednarski et al. | 204/195 |
| 3,902,982 | 9/1975 | Nakagawa | 204/195 |
| 4,049,525 | 9/1977 | Dutton et al. | 204/195 C |
| 4,233,031 | 11/1980 | Matson et al. | 23/230 B |
| 4,786,373 | 11/1988 | Saloheimo et al. | 204/1 |
| 4,913,788 | 4/1990 | Hanulik | 204/105 |

*Primary Examiner*—John Niebling
*Assistant Examiner*—William T. Leader
*Attorney, Agent, or Firm*—Harold M. Dixon; William R. Moser; Richard E. Constant

[57] ABSTRACT

An apparatus and method for electrochemical analysis of elements in solution. An auxiliary electrode 14, a reference electrode 18, and five working electrodes 20, 22, 26, 28, and 30 are positioned in a container 12 containing a sample solution 34. The working electrodes are spaced apart evenly from each other and auxiliary electrode 14 to minimize any inter-electrode interference that may occur during analysis. An electric potential is applied between auxiliary electrode 14 and each of the working electrodes 20, 22, 26, 28, and 30. Simultaneous measurements taken of the current flow through each of the working electrodes for each given potential in a potential range are used for identifying chemical elements present in sample solution 34 and their respective concentrations. Multiple working electrodes enable a more positive identification to be made by providing unique data characteristic of chemical elements present in the sample solution.

5 Claims, 1 Drawing Sheet

VOLTAMETRIC ANALYSIS APPARATUS AND METHOD

The United States Government has rights in this invention pursuant to Contract No. DE-AC09-89SR18035 between the U.S. Department of Energy and Westinghouse Savannah River Company.

BACKGROUND OF THE INVENTION

1. Field of the Invention

The present invention relates to electrochemical analysis of solutions. More particularly, the present invention relates to voltametric identification of concentrations of elements in a sample solution.

2. Discussion of Background

Voltametry is a well known analytical method. Typically, a voltametric analysis, such as stripping analysis, is performed in a measurement cell having three electrodes, namely, an auxiliary electrode, a reference electrode, and a working electrode. The three electrodes are placed in a solution in the measurement cell in spaced-apart arrangement and an electric potential is then applied across the auxiliary electrode and the working electrode. As the potential difference between them is varied over a specific range, a varying current flows through the working electrode as a result of oxidation/reduction reactions of the ions in the sample solution. The voltage/current relationships measured are characteristic of the particular types of substances present in the solution and their concentrations.

The prior art discloses numerous examples of voltametric analysis applications using the conventional three-probe configuration. Banks (U.S. Pat. No. 3,428,532) and Stearn (U.S. Pat. No. 2,531,747) disclose voltametric methods of identifying metal and alloys by using the sample metal of interest as the working electrode in a conventional configuration. In U.S. Pat. No. 3,902,982, Nakagawa discloses a portable apparatus for performing voltametric analysis of city tap water. Also, Saloheimo, et al. (U.S. Pat. No. 4,786,373) disclose a voltametric method that uses the conventional three electrode arrangement with the addition of ultrasonic influences to improve analysis conditions.

Voltametric analysis methods employing nonconventional configurations is believed to be limited. Bednarski, et al. (U.S. Pat. No. 3,859,193) disclose a working electrode that also functions as a rotatable electrolysis cell to allow the analysis to be conducted much faster and with greater accuracy. In another nonconventional arrangement, Dahms (U.S. Pat. No. 3,556,950) discloses a method and apparatus for measuring a plurality of constituents in solution. The apparatus features a plurality of working electrodes, serially arranged, that are responsive to the presence of ions and dissolved gases. The multiple working electrodes are used in succession to assist in the production of voltametric analysis data.

SUMMARY OF THE INVENTION

According to its major aspects and broadly stated, the present invention is an apparatus and method for conducting multiple, simultaneous voltametric analyses using multiple working electrodes to identify a solution by its characteristic potential. The apparatus comprises a plurality of working electrodes, an auxiliary electrode, and a reference electrode in a solution in a cell. The working electrodes are each made of a different material and spaced equal distances from an auxiliary electrode and from each other. Preferably there are five electrodes. By applying the same potential to all five and varying that potential over a preselected range, the current developed in each can identify one or more species present in solution.

A major feature of the present invention is the use of a multiple, different working electrodes. Preferably, five electrodes are used, each one made of a different material. The materials for the electrodes are selected from the following group: carbon, gold, silver, nickel and platinum. Since the electrochemical data generated by a species varies from electrode material to electrode material, a more positive identification of each species can be made. As a consequence of being able to obtain more information characteristic of a particular element, a more precise identification can be made based on that information and the measurement can be made more rapidly.

Another feature of the present invention is the geometric arrangement of the apparatus, to wit: the spacing between the multiple working electrodes, and between the multiple working electrodes and the auxiliary electrode. The spacing between electrodes is equal and the spacing between any one electrode and the auxiliary electrode is equal. This feature minimizes any inter-electrode interference that may occur as the result of positioning more than one working electrode in the same sample solution.

Other features and advantages of the present invention will be apparent to those skilled in the art from a careful reading of the Detailed Description of a Preferred Embodiment presented below and accompanied by the drawings.

DETAILED DESCRIPTION OF A PREFERRED EMBODIMENT

Figure 1:
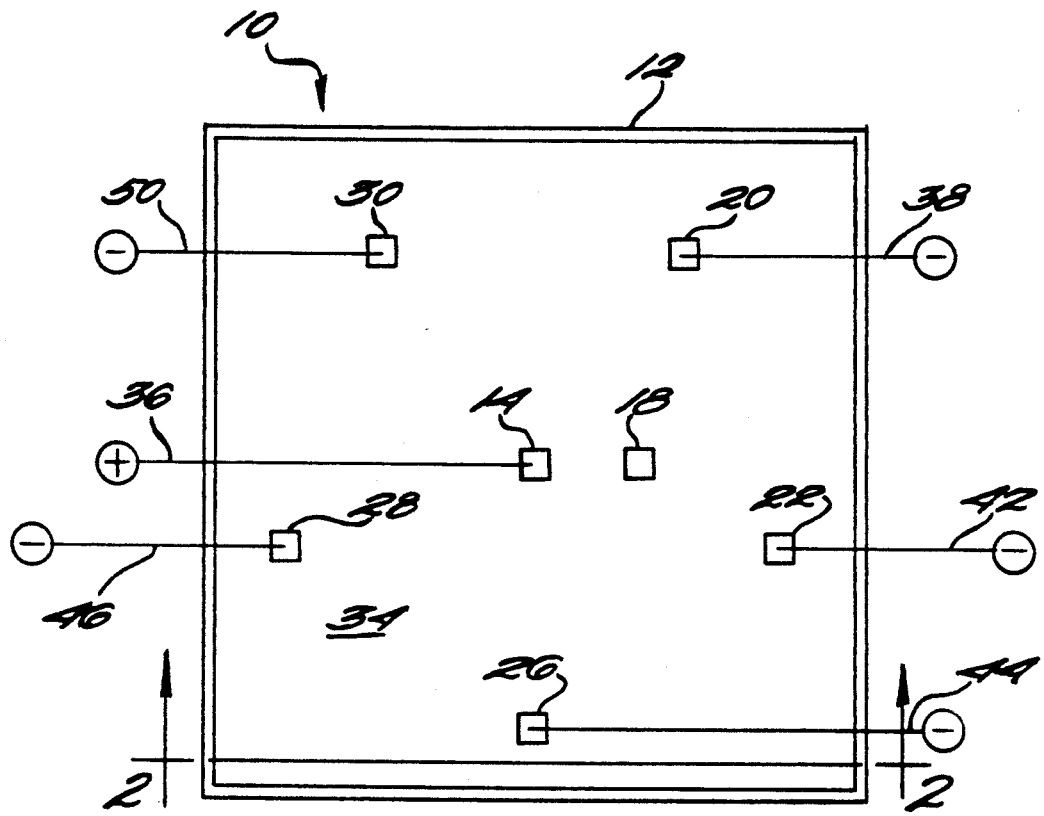
FIG. 1 is a top view of an apparatus and method of voltametric analysis according to a preferred embodiment of the present invention.
Figure 2:
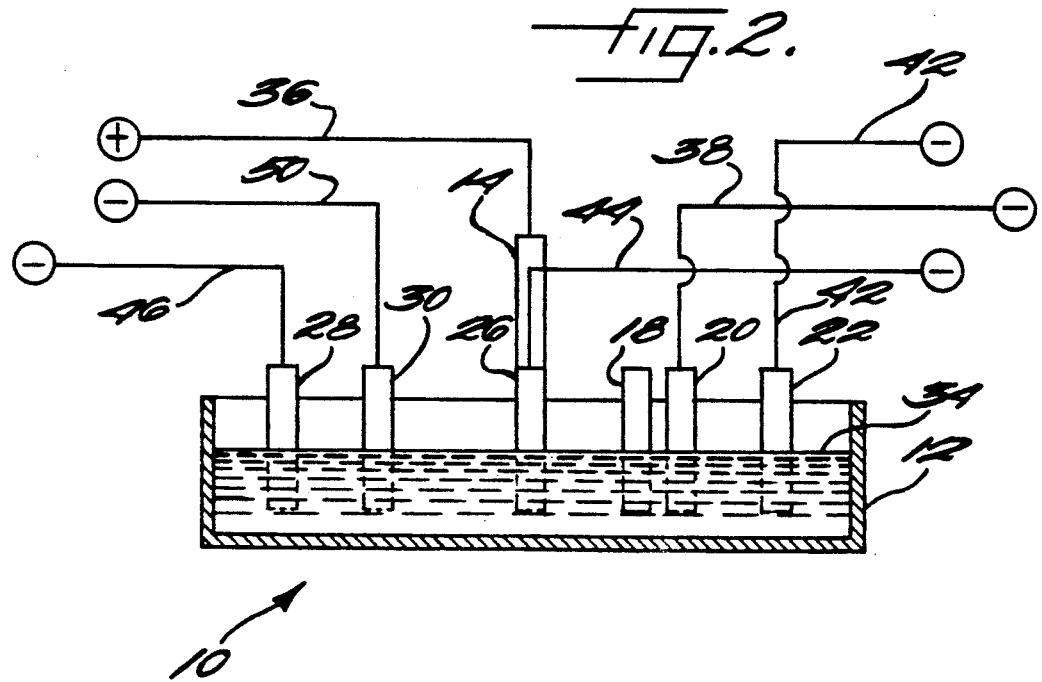
FIG. 2 is a side, cross-sectional view of the apparatus of FIG. 1 taken along lines 2—2.

Referring now to FIG. 1, an apparatus 10 consists of an electrochemical cell 12, an auxiliary electrode 14, a reference electrode 18, and five working electrodes 20, 22, 26, 28, 30. Cell 12 is dimensioned to hold a sample solution 34 (see also FIG. 2) with chemical elements present in the solution. Working electrodes 20, 22, 26, 28, and 30 are each made of a different material, preferably material selected from the group consisting of carbon, gold, nickel, platinum, and silver. For example, working electrode 20 can be made of carbon, working electrode 22 can be made of gold, and so on.

Preferably, each of the working electrodes is separated from each other by the same distance. Similarly, auxiliary electrode 14, which occupies the center of what is essentially a pentagon formed by the five working electrodes defining the "points" of the pentagon, is thus equidistant from each of the working electrodes. The particular electrode orientation is used to minimize any inter-electrode interference among working electrodes that may occur as the result of more than one working electrode simultaneously occupying the same sample solution.

Preferably, reference electrode 18 is positioned adjacent to auxiliary electrode 14, generally spaced an equal distance from each of the working electrodes, and is used in conjunction with a potentiostat to insure the accuracy of the actual voltage potential applied between auxiliary electrode 14 and working electrodes 20, 22, 26, 28, and 30.

In use, auxiliary electrode 14, reference electrode 18, and working electrodes 20, 22, 26, 28, and 30 are positioned in sample solution 34, which is contained in cell 12, generally according to FIG. 1 and the above description. Next, an electrical potential is applied across auxiliary electrode 14 and working electrode 20 using a positive terminal lead 36 and a negative terminal lead 38. Similarly, the same electric potential is established between auxiliary electrode 14 and working electrodes 22, 26, 28, and 30 using positive terminal lead 36 and the negative terminal leads 42, 44, 46, and 50, respectively. Any standard means for measuring current (not shown) can then be connected to each working electrode to determine the amount of current flowing through each.

In a typical analysis procedure, the amplitude of the electric potential between auxiliary electrode 14 and each working electrode is simultaneously varied in discreet steps over a predetermined range of electric potentials. The change in the current flowing through each of the five working electrodes and the actual potential at which this change occurs is measured and recorded. The recorded potentials at which current peaks are characteristic of the chemical elements present in the sample solution (the "characteristic potential"), and the size of a current peak indicates the concentration of the particular chemical element in the sample solution.

Some chemical elements generate similar electrochemical data for a single working electrode made of a particular material, however, it is very rare that two chemical elements generate similar data for five working electrodes, each made of a different material. Therefore, simultaneous analysis using multiple working electrodes, each made of a different material, increases the ability to identify a chemical species because it allows multiple confirmations of the data of any one electrode and it improves resolution when different species produce similar electrochemical data, thereby diminishing the likelihood of confusing one species for another.

It will be apparent to those skilled in the art that many changes and substitutions can be made to the preferred embodiment herein described without departing from the spirit and scope of the present invention as defined by the appended claims.

What is claimed is:

1. Apparatus for analyzing at least one chemical element carried by a solution, said apparatus for use in electrochemical analysis, said apparatus comprising:
    an electrolytic cell dimensioned to hold said solution;
    an auxiliary electrode positioned in said cell; at least five working electrodes positioned in said cell, said at least five working electrodes spaced apart from said auxiliary electrode and each other, each of said at least five working electrodes composed of a different material thereby enabling at least five unique sets of electrochemical data to be generated for said at least one chemical element present in said solution;
    each of the first five of said at least five working electrodes being made of one material selected from the group consisting of carbon, gold, nickel, platinum, and silver;
    means for applying an electrical potential between said auxiliary electrode and each of said at least five working electrodes; and
    means for measuring electrical current flowing through each of said at least five working electrodes.

2. The apparatus as recited in claim 1, wherein said at least five working electrodes are each spaced an equal distance from said auxiliary electrode and from each other.

3. A method for analyzing at least one chemical element, said method comprising the steps of:
    positioning an auxiliary electrode and five working electrodes in a solution carrying said at least one chemical element to be analyzed, said five working electrodes being spaced apart from said auxiliary electrode and each other, said five working electrodes being made of a material selected from the group consisting of carbon, gold, nickel, platinum, and silver; and no two of said five working electrodes being made of the same material;
    simultaneously applying an electrical potential between said auxiliary electrode and each of said five working electrodes; and
    measuring electrical current flowing through each of said five working electrodes.

4. The method as recited in claim 3, wherein said positioning step further comprises spacing said five working electrodes an equal distance from said auxiliary electrode and from each other.

5. The method as recited in claim 3, further comprising the step of varying said potential incrementally within a potential range so that said current through each of said five electrodes changes.

* * * * *